(12) United States Patent
Esfandiari (10) Patent No.: US 10,080,634 B2
(45) Date of Patent: Sep. 25, 2018

(54) DENTAL CURING LIGHT WITH FLEXIBLE TIP

(71) Applicant: S.A.T. INVESTMENT INC., Dollard-des-Ormeaux (CA)

(72) Inventor: Shahrokh Esfandiari, Dollard-des-Ormeaux (CA)

(73) Assignee: S.A.T. INVESTMENT INC., Dollard-des-Ormeaux, Quebec ( * ) Notice: Subject to any disclaimer, the term of this patent is extended or adjusted under 35 U.S.C. 154(b) by 0 days.

(21) Appl. No.: 14/785,481

(22) PCT Filed: Apr. 17, 2014

(86) PCT No.: PCT/CA2014/050384
§ 371 (c)(1),
(2) Date: Oct. 19, 2015

(87) PCT Pub. No.: WO2014/169391
PCT Pub. Date: Oct. 23, 2014

(65) Prior Publication Data
US 2016/0067026 A1 Mar. 10, 2016

Related U.S. Application Data

(60) Provisional application No. 61/813,686, filed on Apr. 19, 2013.

(51) Int. Cl.
*A61C 19/00* (2006.01)
*A61C 13/15* (2006.01)
*A61N 5/06* (2006.01)

(52) U.S. Cl.
CPC .............. *A61C 19/004* (2013.01); *A61N 5/06* (2013.01); *A61N 2005/0651* (2013.01)

(58) Field of Classification Search
CPC ..... A61C 19/004; A61C 19/003; A61C 19/00; A61C 13/14; A61C 1/0007; A61C 1/0015;
(Continued)

(56) References Cited

U.S. PATENT DOCUMENTS

| 6,089,740 A * | 7/2000 | Forehand ............. A61C 19/003 313/634 |
| 2007/0190479 A1* | 8/2007 | Jackson, III ......... A61C 19/004 433/29 |
| 2011/0236851 A1* | 9/2011 | Muller ................. A61C 19/004 433/29 |

FOREIGN PATENT DOCUMENTS

| JP | WO 2005091037 A1 * | 9/2005 | ........... G02B 6/4429 |
| WO | 03051221 | 6/2003 | |

(Continued)

OTHER PUBLICATIONS

International Search Report; PCT/CA2014/050384; dated Jul. 16, 2014.*

*Primary Examiner* — Ralph Lewis
(74) *Attorney, Agent, or Firm* — Norton Rose Fulbright Canada (57) ABSTRACT

A dental curing light for curing a light-cure synthetic composite material used in dentistry is described. The dental curing light includes a hand-held curing light instrument having a curing light source, and a light conducting tip detachably mounted to the hand-held curing light instrument. The light conducting tip has an input end, removably engaged to the hand-held curing light instrument and receiving light from the curing light source, and a remote output end, emitting the curing light therefrom. The light conducting tip has a flexible tubular body extending between the input and output ends, and includes at least a light conducting inner core and a radially outer metallic body surrounding (Continued)

the light conducting inner core. The light conducting inner core forms a flexible optical waveguide. The outer metallic body is flexible and plastically deformable such that the outer metallic body, and therefore the light conducting tip, retains a given curved shape until repositioned by a user.

19 Claims, 6 Drawing Sheets

(58) Field of Classification Search
CPC . A61C 1/0069; A61N 5/06; A61N 2005/0651
USPC ..................................................... 433/28, 29
See application file for complete search history.

(56) References Cited

FOREIGN PATENT DOCUMENTS

| WO | WO 03051221 A1 * | 6/2003 | ............. A61C 1/088 |
|----|------------------|--------|--------------------------|
| WO | 2005091037       | 9/2005 |                          |

* cited by examiner

DENTAL CURING LIGHT WITH FLEXIBLE TIP

CROSS-REFERENCE TO RELATED APPLICATIONS

This application is a National Phase Entry of International Patent Application No. PCT/CA2014/050384 which was filed on Apr. 17, 2014 and claims priority on U.S. Provisional Application No. 61/813,686 which was filed on Apr. 19, 2013, the entire content of each of which is incorporation herein by reference.

TECHNICAL FIELD

The present disclosure relates generally to medical devices, and more particularly to instruments for conducting dental procedures.

BACKGROUND

Composite resins are often used in dentistry applications and procedures, for example as restorative material or adhesives. Such composite resins are often synthetic resins, which became popular for use as restorative materials because of favourable properties such as insolubility, ease of manipulation, etc. Synthetic resins which are "light cured" are also now relatively common. These light-cured synthetic resin-based composites are typically cured using a dental curing light.

Several different types of dental curing lights exist. All of such known dental curing lights are used to polymerize light-cured synthetic resin-based composites for dentistry applications. Known dental curing lights include employ, for example, laser, plasma arc curing (PAC), Tungsten halogen and light-emitting diode (LED) systems for curing the synthetic composites. LED based dental curing lights are, at present, most commonly used.

However, there exist disadvantages with the LED curing lights that are currently known and employed in dentistry applications. All of these curing lights typically employ a similar LED light-source and have short rigid tips from which the light is emitted. However, such known LED curing lights can be difficult to manipulate into a comfortable position for the dentist, and provide little to no adjustability or flexibility in terms of position of the instrument. Thus, known curing lights fall short in terms of delivering proper accessibility. As a result, dentists or other users of these devices therefore sometimes need to raise their hands/shoulders into uncomfortable positions, making regular and continued use of such products undesirable. Over time, chronic muscle fatigue or other undesirable issues resulting from the use of these products can occur.

SUMMARY

Accordingly, there is provided an improved dental curing light, an improved tip for such a dental curing light, and/or an improved method of curing light-cure synthetic composite materials during a dental procedure.

In accordance with one aspect of the present invention, there is provided a dental curing light for curing light-cure synthetic composite materials used in dentistry, comprising: a hand-held curing light instrument having a curing light source; and a light conducting tip detachably mounted to the hand-held curing light instrument, the light conducting tip having an input end and a remote output end, the input end of the light conducting tip being removably engaged to the hand-held curing light instrument and receiving light from the curing light source, the remote output end of the light conducting tip emitting the curing light therefrom, the light conducting tip having a flexible tubular body extending between the input and output ends thereof, the flexible tubular body including at least a light conducting inner core and a radially outer metallic body surrounding the light conducting inner core, the light conducting inner core forming a flexible optical waveguide, the outer metallic body being substantially light impervious and fluid impervious, the outer metallic body being flexible and plastically deformable such that the outer metallic body, and therefore the light conducting tip, retains a given curved shape until repositioned by a user.

There is also provided, in accordance with another aspect of the present invention, a light conducting tip for a hand-held dental curing light which emits a light emitting diode (LED) light to cure a synthetic composite dental material by polymerization, the light conducting tip comprising: an input end including at least a portion of a releasable engagement mechanism for detachably mounting the light conducting tip to the hand-held dental curing light, the input end having an optical input for receiving the LED light into the light conducting tip from the hand-held dental curing light; a remote output end spaced apart from the first end and having an optical output which emits the LED light therefrom; and a flexible tubular body extending between the input end and the output end, the elongated tubular body having a light conducting core extending a length of the light conducting tip, the flexible tubular body including at least a light conducting inner core and a radially outer metallic body surrounding the light conducting inner core, the light conducting inner core providing an optical waveguide which is in optical communication with both the optical input and the optical output and which transmits the LED light therebetween, the outer metallic body being substantially light impervious and fluid impervious, the outer metallic body being flexible and plastically deformable such that the outer metallic body retains a given curved shape; wherein the flexible tubular body is configured to be bent into a curved shape and is plastically deformable to enable the light conducting tip to retain said curved shape until repositioned by the user.

There is further provided, in accordance with another aspect of the present invention, a method of curing a light-cure synthetic composite material during a dental procedure, comprising: affixing a detachable light conducting tip to a hand-held curing light instrument operable to produce a curing light, the light conducting tip having a flexible tubular body that is selectively positionable in any number of different curved configurations; bending the flexible tubular body of the light conducting tip into a desired curved configuration, the flexible tubular body of the light conducting tip maintaining said desired curved configuration until being repositioned; positioning a light-emitting output end of the light conducting tip proximate to a site having the light-cure synthetic composite material; and activating the hand-held curing light instrument to emit said curing light from the light-emitting output end of the light conducting tip, the curing light being transmitted through the desired curved configuration of the flexible tubular body of the light conducting tip.

BRIEF DESCRIPTION OF THE DRAWINGS

Reference is now made to the accompanying drawings, showing by way of illustration a preferred embodiment thereof, and in which.

DETAILED DESCRIPTION

Figure 1:
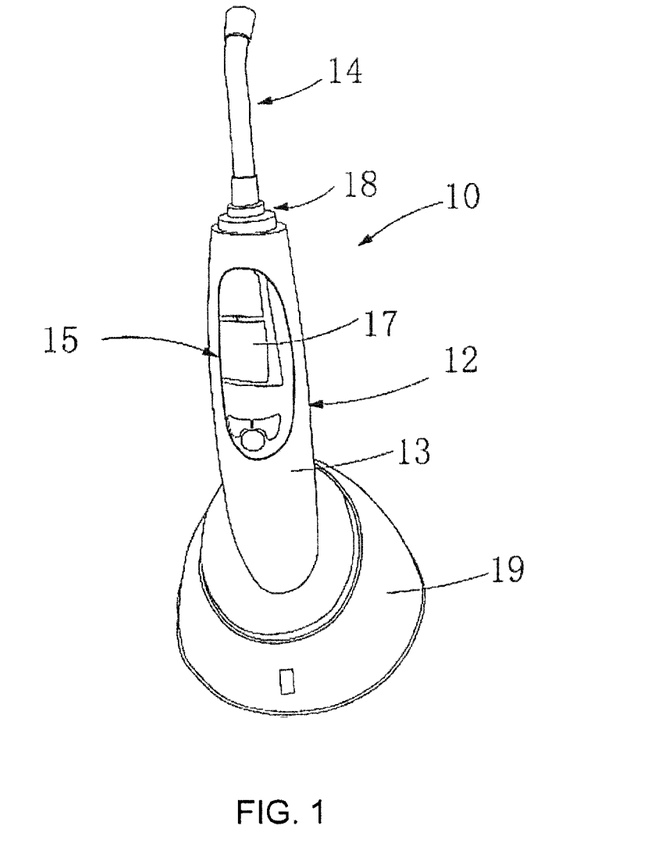
FIG. 1 is a perspective view of a dental curing light in accordance with the present disclosure, having a flexible tip portion.

Referring to FIG. 1, the dental curing light 10 of the present disclosure includes generally a hand-held dental curing light instrument 12 having a light conducting wand, or tip, 14 which is mounted thereto.

The hand-held dental curing light instrument 12 includes therein a curing light source, which may be a light emitting diode (LED) or another type of suitable curing light source, such as but not limited to laser, plasma arc curing (PAC) and Tungsten halogen light sources, for example.

In a particular embodiment, the light source used for the present dental curing light 10 is a LED light source. One advantage of using an LED light source is that it remains cold, in that little to no temperature rise occurs during operation of the instrument 12 and thus during the light curing process. In at least one particular embodiment, the LED "light engine" of the curing light instrument 12 of the present dental curing light 10 has a 5 watt (W) power capacity, produces a maximum light intensity of about 2200 me/cm using the 5 W LED, and has a wavelength range of between 430 nanometers (nm) and 490 nm, with a peak at 460 nm. This particular wavelength range ensures correct and efficient polymerization during the curing of the light cure dental materials. In at least one embodiment, the working voltage of the present curing light instrument 12 is from 100-240 volts (V) AC, at 50-60 Hz, in order to ensure as universal use as possible.

The hand-held dental curing light instrument 12 includes generally a hand grip portion 13 and user actuated controls 15 thereon, which may include one or more buttons or switches (three control buttons are shown in the depicted embodiment of FIG. 1) used to operate the hand-held curing light instrument 12 of the dental curing light 10. The instrument 12 may also include an LCD screen 17 or other display device(s) disposed directly on the handle of the device, which provides information to the user of the device, such as duration of operation, wavelength of light emitted, etc. The user actuated controls 15 are in communication with an electronic control unit disposed within the hand-held instrument 12, and which may include processor and a memory storage unit, and signal producing means including both visual signals, such as lights, on-screen displays, etc, as well as audible signals. For example, in one embodiment, the control system is configured to produce an audible signal (such as a "beep") at predetermined, and adjustable, intervals, and/or to sound an audible signal after a pre-determined duration of time during which the dental curing light 10 has been emitting light, such as to accurately control the curing time during which the materials are exposed to the curing light produced by the device 10. The LCD screen 17 may also provide this information. Such audible alert can be used to notify the operator of the device of the elapsed time of light emission, thereby facilitation incremental composite layer fillings.

Further, the controls 15 may also permit the power output of the emitted light to be adjusted, such that it can be modified as required. In this regard, in one particular embodiment, the control system of the instrument 12 is programmed to have at least three (3) different curing modes, including the following: 1) mode 1 is a "full mode", wherein a full power output is provided during the entire determined treatment period; 2) mode 2 is a "ramp up mode", wherein the power output gradually increases from 30% to 100% during the first third of the treatment and then stays at 100% for the balance (two thirds) of the treatment period; and 3) mode 3 is a "pulse mode", wherein light power output goes from zero to full power for half a second and then remains off for the three subsequent seconds. Other embodiments and variations of treatment period and power output are also possible, and can be varied, controlled and set as desired. An additional "auto off" feature may also be included, whereby the device automatically turns itself off after a predetermined period of time in use (such as 30 seconds, for example).

As seen in FIG. 1, the hand-held instrument 12 of the dental curing light 10 may be powered by a rechargeable battery contained therein, which may be re-charged when not in use by placing the instrument 12 into a recharging cradle 19. In one particular embodiment, an alert (visual and/or audible) is provided to the user when the battery level is low.

The light conducting tip 14 of the dental curing light 10 is mounted to the hand-held dental curing light instrument 12 in optical communication therewith. In the embodiment described and depicted herein, the light conducting tip 14 is detachably mounted to the hand-held instrument 12, such that the tip 14 can be removed when desired from the hand-held instrument 12 when not in use.

However, it is to be understood that this is not necessary, and that the flexible tip 14 as described herein may, in an alternate embodiment, be permanently fixed to the hand-held portion 13 of the instrument 12. Regardless, in the embodiment described herein where the tip 14 is detachably mounted to the hand-held instrument 12, this enables the tip 14 to be replaceable and/or to be removed during storage, transport, and the like.

When the dental curing light is to be used, the tip 14 is engaged in place on the hand-held dental curing light instrument 12. A releasable engagement mechanism 18 is thus provided for detachably mounting the tip 14 to the hand-held instrument 12, at least a portion of which is disposed on one end of the tip 14 and the other mating or cooperating portion of which is disposed on the output end of the instrument 12. This releasable engagement mechanism 18 may include, for example, quick-connect type fastening/release mechanisms, such as a luer-lock connection, a threaded connection, or a combination of one or more of such mechanisms. The coupling mechanism 18 may also permit the flexible tip 14 to be interchanged with other tips, such as rigid tips or alternate flexible tip designs.

Figure 2A:
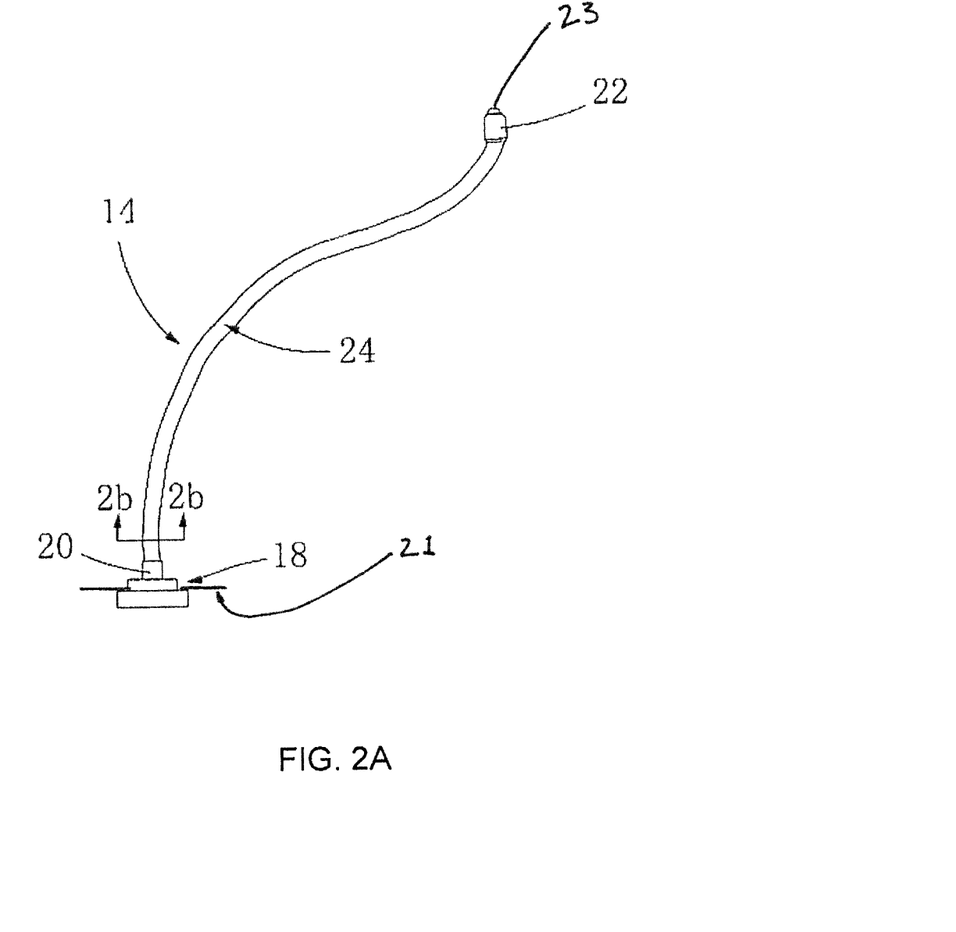
FIG. 2A is a schematic side view of a flexible tip portion of the dental curing light of FIG. 1.
Figure 2B:
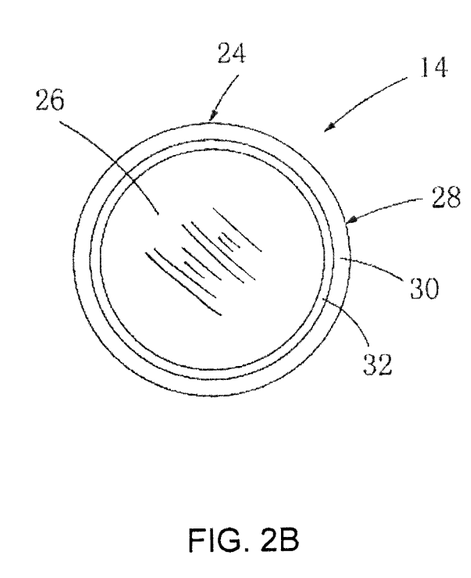
FIG. 2B is a cross-sectional view of the flexible tip of FIG. 2A, taken through line 2B-2B.

Referring now to the light conducting tip 14 in more detail and with reference to FIGS. 2A-2B, the light conducting tip 14 includes an input end 20 and a remote output end 22. The input end 20 is removably engaged to the hand-held curing light instrument 12 via the releasable engagement mechanism 18 and therefore, when so connected, is positioned and/or aligned such as to receive the light from the curing light source within the hand-held dental curing light instrument 12. The input end 20 therefore has an optical input for receiving the light (LED or otherwise) from the instrument 12, and the remote output end 22 of the light conducting tip 14 has an optical output which emits the curing light therefrom when the device is activated. In one possible embodiment, although not necessarily required, the remote output end 22 may also include a lens 23 or other light focusing device.

The light conducting tip 14 has a generally tubular and elongated body 24, which extends between the input end 20 and the output end 22 and which is "flexible", as will be described in further detail below. The term "flexible" as used herein is understood to mean non-rigid and thus bendable or repositionable into any number of different shapes (e.g. curved or otherwise), without causing any significant damage to the body. Additionally, the flexible body 24 as described herein is plastically deformable and thus configured so as to retain its given bent shape or curved configuration until such time as it is manually re-positioned by the user.

The flexible body 24 of the light conducting tip 14 has a light conducting core 26 therein which extends the complete length of the light conducting tip, namely from the input end 20 to the output end 22 thereof. The light conducting core 26 provides an optical waveguide which is in optical communication with both the optical input and the optical output at the input and output ends 20 and 22 respectively, and which transmits the curing light along the full length of the body 24. As noted above, and as shown in FIG. 2, the elongated body 24 of the light conducting tip 14 is flexible, and it is therefore able to be readily bent into any desired curved shape by a user, without requiring the use of any significant force or tools. The body 24 of the light conducting tip 14 is thus sufficiently flexible to enable it being bent into a desired curved shape. Further, unlike many thin optical waveguides or typical fibre optic wires, the body 24 of the light conducting tip 14 is plastically deformable, in that it retains any curved shape given to it until such time as it is repositioned by a user. The flexible body 24 of the light conducting tip 14 is therefore configured for and operable to retain its given shape (i.e. when bent or curved, it will stay in position), which may be curved, bent, straight or any combination thereof, until repositioned by a user.

Referring now to FIG. 2B, the specific configuration of the flexible tip 14 will now be described in further detail. Although several different specific constructions of the flexible tip 14 are possible, in one particular embodiment the body 24 of the flexible tip 14 is composed of an outer main body 28 and the light conducting core 26. The outer main body 28 may be metallic, and may comprise a metallic outer braiding 30 (made of #304 stainless steel wire, for example) which surrounds an inner conduit 32 made of galvanized steel having a PVC or silicone outer jacket. The outer main body 28 may also comprise a "gooseneck" type configuration. This outer main body 28 is highly flexible, liquid tight and substantially light impervious. The metallic outer braiding 30 may also comprise foam and/or rubber covered wire arms, and super-flex steel alloy wires. It is the outer main body 28 which enables the tip 14 to be both flexible and to retain its position once curved into the desired shape. The light conducting core 26 which serves as an optical wave guide is flexible without any loss of light transmission, without being itself plastically deformable (i.e. the optical wave guide formed by the light conducting core 26 is itself flexible but elastically deformable, and thus is held in position by the plastically deformable outer main body 28 of the flexible tip 14). The light conducting core 26 may comprise a bundle of optical fibres which transfer the light therethrough.

In at least one possible embodiment, the flexible tip 14 includes a hollow wire inner construction composed of a super flex steel alloy, and may be completely encapsulated and covered in soft silicone/PVC or a similar material. Although various lengths of tips may be used, in one embodiment the tip 14 has an unbent length of about 6 inches. Much as for the instrument 12, the tip 14 may also be easily wiped clean after use, for disinfection purposes.

In one particular embodiment, the dental curing light 10 may also include a protective shield 21 (see FIG. 2A) mounted at the base of the tip at the input end 20, between the flexible tip 14 and the hand-held instrument 12. This protective shield 21 may be circular in shape, for example, and project radially out from the base of the tip 14. This protective shield may also be removably mounted to the instrument 12, such as to enable ease of cleaning, installation and shipping of the product for example.

Accordingly, during use, the present dental curing light 10 is used to cure a light-cure synthetic composite dentistry material during a dental procedure. This process may include, for example, the steps of: providing the dental curing light 10 having a hand-held instrument 12 and a flexible light conducting tip 14 as described above; bending the flexible body of the light conducting tip into a desired curved configuration such that the flexible body 24 of the light conducting tip 14 maintains the desired curved configuration; positioning the light-emitting output end 22 of the light conducting tip 14 proximate to a site having the light-cure synthetic composite dentistry materials therein; and activating the dental curing light to emit curing light from the light-emitting output end 22 of the light conducting tip 14.

The flexible light conducting tip 14 accordingly delivers the dental curing light (which may be LED light for example), and is bendable and malleable into any desired shape or configuration (which may be typically, but is not limited to, a curved or compound curved shape). This increased flexibility provides improved accessibility to all teeth surfaces, and makes use of the device more comfortable for the dentist, dental hygienist or user of the device, as the most comfortable hand and/or shoulder position can be chosen and the flexible tip 14 can be bent accordingly to accommodate this position while maintaining the light on the teeth surfaces to be cured. This may particularly enable improved access to the posterior teeth, as once the flexible tip 14 is bent into a desired curved shape such as to access buccal, lingual and/or proximal sides of the posterior teeth, the user of the device need not raise his or her hands, elbows and/or shoulders to correctly position the curing light over the surfaces to be cured.

The entire instrument 12 and the tip 14 of the present curing light 10 is designed to be grip-friendly, and to have a suitable weight for ease of operation. The hand grip portion 13 of the instrument 12 may include silicon cover therein, for improved grip and comfort. Both the hand-held instrument 12 and the flexible tip 14 are also easily cleaned and disinfected.

Figure 3:
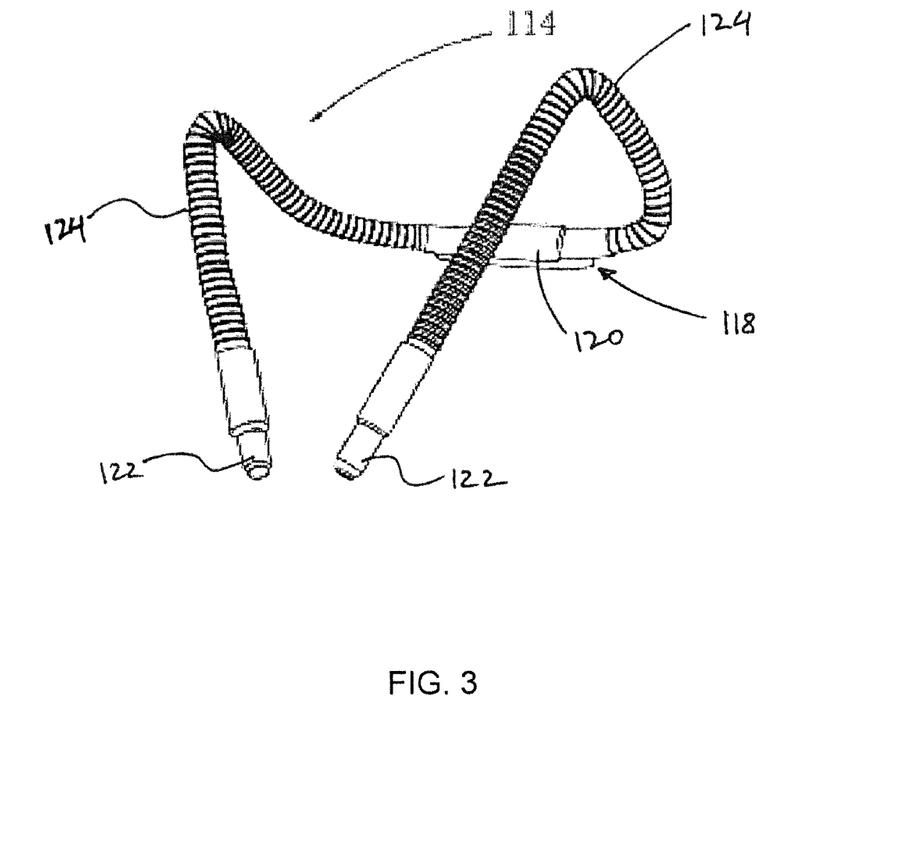
FIG. 3 is a perspective view of an alternate flexible tip portion in accordance with another embodiment of the present disclosure.
Figure 4:
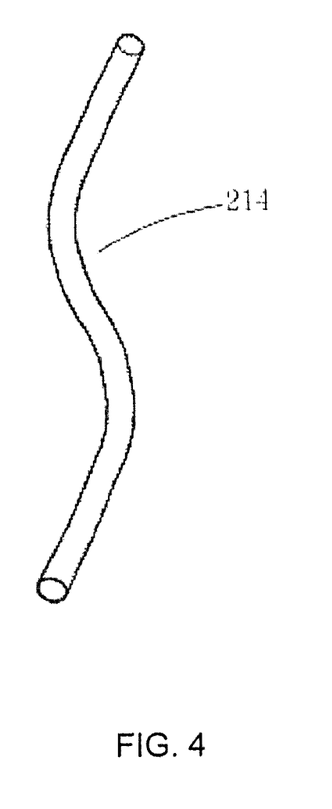
FIG. 4 is a perspective view of another alternate flexible tip portion in accordance with another embodiment of the present disclosure.
Figure 5:
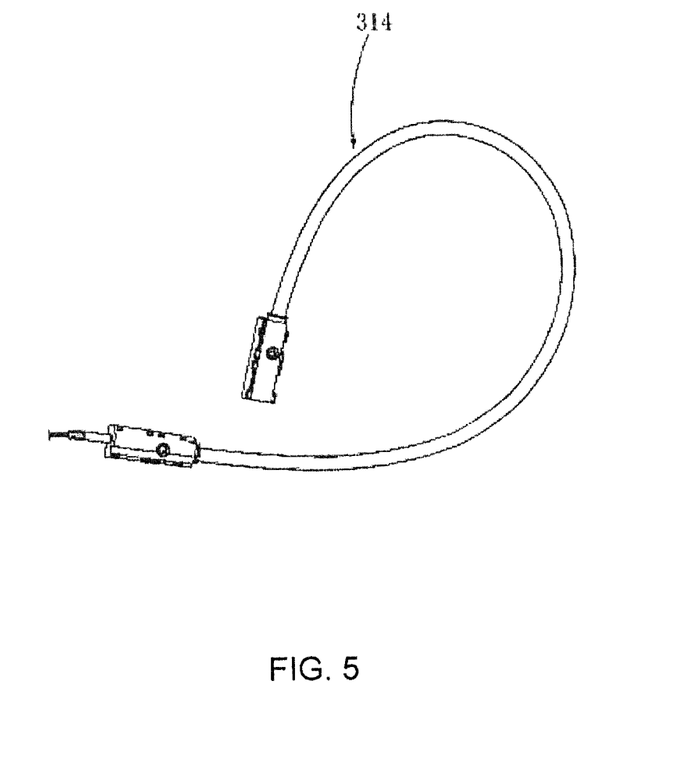
FIG. 5 is a perspective view of a further alternate flexible tip portion in accordance with another embodiment of the present disclosure.

FIGS. 3-5 depict alternate flexible tip portions 114, 214 and 314 in accordance with other possible embodiments of the present disclosure. Each of the flexible tip portions 114, 214 and 314 is configured to be mounted, either detachably or fixed, to the hand-held curing light instrument 12 as described above.

The flexible tip 114 of FIG. 3 comprise two separate flexible bodies 124 through which curing light is directed to two separate output ends 122. A common input end 120 receiving the light from the light source of the handheld instrument 12, and similarly includes an attachment mechanism 118 for removable mounting of the tip 114 to the instrument 12. Accordingly, the "two-headed" flexible tip 114 may be used so as to simultaneously providing curing light to two different locations in the mouth, or alternately so as to direct the curing light to the same target location from two different (e.g. opposed) directions.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A dental curing light for curing light-cure synthetic composite materials used in dentistry, comprising:
   a hand-held curing light instrument having a curing light source including a light emitting diode (LED) light engine; and
   a light conducting tip detachably mounted to the hand-held curing light instrument, the light conducting tip having an input end and a remote output end, the input end of the light conducting tip being removably engaged to the hand-held curing light instrument and receiving a curing light from the LED light engine, the remote output end of the light conducting tip emitting the curing light therefrom, the light conducting tip having a flexible tubular body extending between the input and output ends thereof, the flexible tubular body including at least a light conducting inner core forming a flexible optical waveguide without being plastically deformable, and an outer metallic body having a metallic outer braiding and a metallic inner conduit disposed radially inwardly from the metallic outer braiding, the metallic inner conduit being disposed between the metallic outer braiding and the light conducting core, the metallic outer braiding being substantially light impervious and fluid impervious, the outer metallic body being flexible and plastically deformable such that the outer metallic body, and therefore the light conducting tip, retains a given curved shape until repositioned by a user.

2. The dental curing light of claim 1, wherein the metallic outer braiding is composed of stainless steel wire.

3. The dental curing light of claim 1, wherein the metallic inner conduit is composed of flexible galvanized steel tubing.

4. The dental curing light of claim 3, wherein the galvanized steel tubing has a PVC or silicone outer jacket.

5. The dental curing light of claim 1, wherein the metallic outer braiding is coated in foam or rubber.

6. The dental curing light of claim 1, wherein the metallic outer braiding is composed of super-flex steel alloy wires.

7. The dental curing light as defined in claim 1, wherein the LED light engine produces light having a wavelength range of between 430 nanometers and 490 nanometers, and the light conducting inner core of the light conducting tip is operable to transmit light having a wavelength within said wavelength range.

8. The dental curing light as defined in claim 1, wherein the curing light source has a 5 watt power capacity and produces a maximum light intensity of about 2200 me/cm.

9. The dental curing light as defined in claim 1, wherein the flexible tubular body includes two separate flexible body members each extending from the common input end of the light conducting tip to a separate output end, each flexible body member receiving a curing light from the LED light engine via the input end of the light conducting tip, the remote output end of each flexible body member emitting the curing light therefrom.

10. A light conducting tip for a hand-held dental curing light which emits a light emitting diode (LED) light to cure a synthetic composite dental material by polymerization, the light conducting tip comprising:
   an input end including at least a portion of a releasable engagement mechanism for detachably mounting the light conducting tip to the hand-held dental curing light, the input end having an optical input for receiving the LED light into the light conducting tip from the hand-held dental curing light;
   a remote output end spaced apart from the first end and having an optical output which emits the LED light therefrom; and
   a flexible tubular body extending between the input end and the output end, the elongated tubular body having a light conducting core extending a length of the light conducting tip, the flexible tubular body including at least a light conducting inner core forming a flexible optical waveguide without being plastically deformable which is in optical communication with both the optical input and the optical output and which transmits the LED light therebetween, the flexible tubular body including an outer metallic body having a metallic outer braiding and a metallic inner conduit disposed radially inwardly from the metallic outer braiding, the metallic inner conduit being disposed between the metallic outer braiding and the light conducting core, the metallic outer braiding being substantially light impervious and fluid impervious, the outer metallic body being flexible and plastically deformable such that the outer metallic body, and therefore the flexible tubular body, retains a given curved shape until repositioned by the user.

11. The light conducting tip of claim 10, wherein the metallic outer braiding is composed of stainless steel wire.

12. The light conducting tip of claim 10, wherein the metallic inner conduit is composed of flexible galvanized steel tubing.

13. The light conducting tip of claim 12, wherein the galvanized steel tubing has a PVC or silicone outer jacket.

14. The light conducting tip of claim 10, wherein the metallic outer braiding is coated in foam or rubber.

15. The light conducting tip of claim 10, wherein the metallic outer braiding is composed of super-flex steel alloy wires.

16. The light conducting tip as defined in claim 10, wherein the LED light has a wavelength range of between 430 nanometers and 490 nanometers, and the light conducting inner core is operable to transmit light having a wavelength within said wavelength range.

17. The light conducting tip as defined in claim 10, wherein the hand-held dental curing light has a 5 watt power capacity and produces a maximum light intensity of about 2200 me/cm.

18. The light conducting tip as defined in claim 10, wherein the flexible tubular body includes two separate flexible body members each extending from the common input end of the light conducting tip to a separate output end, each flexible body member receiving a curing light from the LED light engine via the input end of the light conducting tip, the remote output end of each flexible body member emitting the curing light therefrom.

19. A method of curing a light-cure synthetic composite material during a dental procedure, comprising:

affixing a detachable light conducting tip to a hand-held curing light instrument operable to produce a curing light with a light emitting diode (LED), the light conducting tip having a flexible tubular body with an outer metallic body that is selectively positionable in any number of different curved configurations;

plastically deforming the outer metallic body of the flexible tubular body of the light conducting tip into a desired curved configuration, the flexible tubular body of the light conducting tip maintaining said desired curved configuration until being repositioned;

positioning a light-emitting output end of the light conducting tip proximate to a site having the light-cure synthetic composite material; and activating the hand-held curing light instrument to emit said curing light from the light-emitting output end of the light conducting tip, the curing light being transmitted through the desired curved configuration of the flexible tubular body of the light conducting tip.

* * * * *